United States Patent [19]

Marconi et al.

[11] Patent Number: 4,591,596

[45] Date of Patent: May 27, 1986

[54] TREATING PAIN, INFLAMMATION AND/OR PLATELET AGGREGATION

[75] Inventors: Walter Marconi, San Donato Milanese; Francesco Bartoli, Rome; Franco Morisi, Rome; Francesco Pittalis, Rome, all of Italy

[73] Assignee: E.N.I. Ente Nazionale Idrocarburi, Rome, Italy

[21] Appl. No.: 552,987

[22] Filed: Nov. 17, 1983

Related U.S. Application Data

[63] Continuation of Ser. No. 336,828, Jan. 24, 1982, which is a continuation-in-part of Ser. No. 227,386, Jan. 22, 1981, abandoned, which is a continuation of Ser. No. 85,015, Oct. 15, 1979, abandoned.

[30] Foreign Application Priority Data

Oct. 17, 1978 [IT] Italy ................................. 28825 A/78

[51] Int. Cl.$^4$ ............................................. A61U 31/42
[52] U.S. Cl. ..................................................... 514/375
[58] Field of Search ........................ 514/374, 377, 375

[56] References Cited

FOREIGN PATENT DOCUMENTS 2942050 4/1980 Fed. Rep. of Germany .

OTHER PUBLICATIONS

Instituto Farmacologico Serono S.p.A., "Chem. Abstracts", vol. 71, 1969, 70587m.

Primary Examiner—Stanley J. Friedman
Attorney, Agent, or Firm—Morgan, Finnegan, Pine, Foley & Lee

[57] ABSTRACT

This invention relates to chemical products of general formula

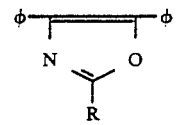

wherein R is an amino group, mono or bi-hydroxyalkyl substituted, or a thio group, mono hydroxyalkyl substituted, in which one or more of the available —OH groups have been esterified with acids containing 2 to 18 carbon atoms.

It is also described a process for the preparation of said products, which comprises reacting a corresponding starting compound, N or S-hydroxyalkyl substituted, with the chloride or the anhydride of the acid concerned.

8 Claims, No Drawings

TREATING PAIN, INFLAMMATION AND/OR PLATELET AGGREGATION

This is a continuation of application Ser. No. 336,828 filed Jan. 24, 1982 which is a continuation-in-part of Ser. No. 227,386 filed Jan. 22, 1981, abandoned, which in turn is a continuation application of Ser. No. 85,015, filed Oct. 15, 1979, now abandoned.

This invention relates to a series of 2-amino or 2-thio substituted derivatives of 4,5-diphenyl-oxazole, and the process for their preparation.

These derivatives are represented by the general formula

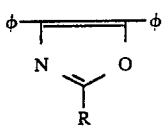

in which R is a mono or bihydroxyalkyl substituted amino group or a mono hydroxyalkyl substituted thio group, and in which one or more available —OH groups have been esterified with saturated or unsaturated acids containing 2 to 18 carbon atoms.

The preparation method consists of reacting the N-hydroxyalkyl substituted compound at ambient temperature in a suitable solvent (acetone, benzene, toluene, xylene) with the acid chloride or the anhydride of the acid of which it is required to obtain the ester, in the presence of a base acting as an acceptor of the acid developed (e.g. triethylamine, pyridine). The product obtained is separated and purified by chromatography through a silica gel column using a suitable eluent system. These products can be used in the pharmaceutical industry, or as intermediates in organic synthesis.

The method of preparing these derivatives is described in detail by the following examples, which however are not to be considered as limiting the invention.

EXAMPLE 1

4,5-diphenyl-2-(2-hydroxyethyl,2'-ethyl acetate)-amino oxazole

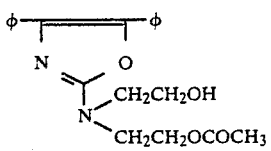

10 g of 4,5-diphenyl-2-bis-(2-hydroxyethyl)-amino oxazole of formula:

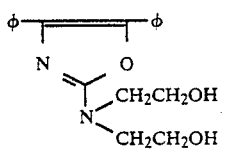

were dissolved in 10 ml of anhydrous acetone.

3 g of acetyl chloride and 4 g of triethylamine were added to the solution. After a few minutes at ambient temperature, a precipitate of triethylammonium chloride forms. A volume of ethyl ether is added to the reaction mixture after about 1 hour. This facilitates the precipitation of all the triethylammonium salt which is formed as a result of the reaction.

The clear solution is concentrated and passed through a silica gel column using 65:35 toluene/acetone as the eluent system.

Three fractions are obtained on elution.

The second fraction is evaporated to dryness with a vacuum pump, and a weakly yellow coloured oil is obtained which after a certain time solidifies to give a white solid having a melting point of 77°–78° C. Spectroscopic and elementary analyses confirm that the product obtained is 4,5-diphenyl-2-(2-hydroxyethyl,2'-ethyl acetate)-amino oxazole. Yield 71%.

EXAMPLE 2

4,5-diphenyl-2-bis(2-ethyl acetate)-amino oxazole

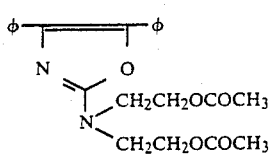

10 g of 4,5-diphenyl-2-bis(2-hydroxyethyl)-amino oxazole were dissolved in 10 ml of anhydrous acetone. 9 g of acetyl chloride and 8 g of triethylamine were added to the solution. The mixture reacted for about 1 hour at ambient temperature. The formation of a precipitate of triethyalmmonium chloride was observed. At the end of the reaction, the precipitation of the salt was completed by adding a volume of ethyl ether. The clear solution obtained was finally concentrated and passed through a silica gel column and eluted with the 65:35 toluene/acetone system. Three fractions are obtained, the first of which, the most abundant, is evaporated to dryness with a vacuum pump. The yellow oil obtained solidifies after a few days, to give a white solid having a melting point of 44°–45° C. Spectrophotometric and elementary analyses carried out on the powder confirm that the product obtained is 4,5-diphenyl-2-bis(2-ethyl acetate)-amino oxazole.

Yield 73%.

EXAMPLE 3

4,5-diphenyl-2(2-hydroxyethyl,2'-ethyl propionate)-amino oxazole

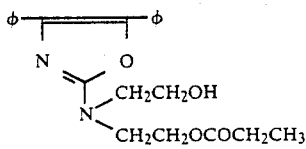

10 g of 4,5-diphenyl-2-bis(2-hydroxyethyl)-amino oxazole were dissolved in 10 ml of anhydrous acetone. 3.5 g of propionyl chloride and 4 g of triethylamine were added to the solution. After about 1 hour, the precipitated triethylammonium chloride is separated by filtration. The clear liquid is concentrated and passed through a silica gel column using 65:35 toluene/acetone as the eluent system. On elution, three fractions are obtained. The second fraction consisting of the 4,5-diphenyl-2-(2-hydroxyethyl,2'-ethyl propionate)-amino oxazole is evaporated to dryness with the vacuum pump to give a yellow oil.

Yield 69%.

EXAMPLE 4

4,5-diphenyl-2-bis(2-ethyl propionate)-amino oxazole

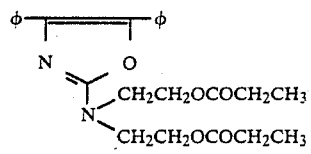

10 g of 4,5-diphenyl-2-bis(2-hydroxyethyl)-amino oxazole were dissolved in 10 ml of anhydrous acetone. 10 g of propionyl chloride and 8 g of triethylamine were added to the solution. After 1 hour of reaction, the solution is filtered and concentrated. The product is purified by passing through a silica gel column and eluting with 65:35 v/v toluene/acetone. The fraction consisting of 4,5-diphenyl-2-bis(2-ethyl propionate)-amino oxazole is evaporated to dryness and a viscous oil is obtained.

Yield 74%.

EXAMPLE 5

4,5-diphenyl-2-(2-hydroxyethyl,2'-ethyl oleate)-amino oxazole

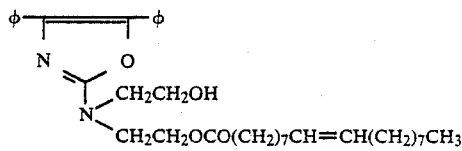

10 g of 4,5-diphenyl-2-(2-hydroxyethyl)-amino oxazole were dissolved in 10 ml of anhydrous acetone. 10 g of oleyl chloride and 4 g of triethylamine were added to the solution.

It is filtered after 1 hour of reaction at ambient temperature, and the solution concentrated. The product is purified by passage through a silica gel column, eluting with 65:35 toluene/acetone. The fraction containing the 4,5-diphenyl-2-(2-hydroxyethyl,2'-ethyl oleate)-amino oxazole is evaporated to dryness to give a yellow oil. Yield 77%.

EXAMPLE 6

4,5-diphenyl-2-bis(2-ethyl oleate)-amino oxazole.

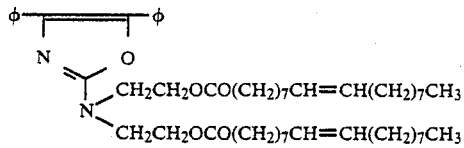

10 g of 4,5-diphenyl-2-bis(2-hydroxyethyl)-amino oxazole are dissolved in 10 ml of anhydrous acetone together with 30 g of oleyl chloride and 8 g of triethylamine. It is filtered after two hours of reaction at ambient temperature, and the product in the solution is purified by passing it through a silica gel column. It is eluted with 65:35 toluene/acetone. The fraction containing the 4,5-diphenyl-2-bis(2-ethyl oleate)-amino oxazole is dried under vacuum to give a yellow oily residue. Yield 72%.

EXAMPLE 7

4,5-diphenyl-2-(2-ethyl acetate)-thio oxazole

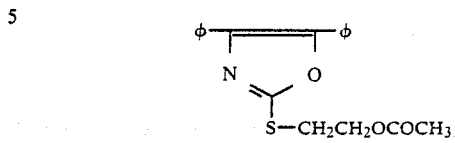

10 g of 4,5-diphenyl-2-(2-hydroxyethyl)-thio oxazole of formula

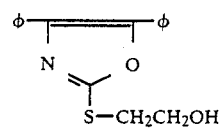

are dissolved in 10 ml of anhydrous acetone. 3 g of acetyl chloride and 4 g of triethylamine are added to the solution. It is filtered after one hour of reaction at ambient temperature, and the solution is concentrated. It is purified by silica gel chromatography, eluting with 80:20 toluene/acetone. The fraction containing the 4,5-diphenyl-2-(2-ethyl acetate)-thio oxazole is evaporated to dryness.

The oily residue crystallises after a few days to give a white powder having a melting point of 96°–98° C. Yield 75%.

EXAMPLE 8

4,5-diphenyl-2-(2-ethyl propionate)-thio oxazole

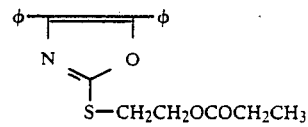

10 g of 4,5-diphenyl-2-(2-hydroxyethyl)-thio oxazole were dissolved in 10 ml of anhydrous acetone. 3.5 g of propionyl chloride and 4 g of triethylamine were added to the solution. After one hour of reaction the solution was filtered and concentrated.

The product was purified by elution through a silica gel column, using 80:20 toluene/acetone as eluent. The product was obtained as a viscous oil on evaporating to dryness the fraction containing the 4,5-diphenyl-2-(2-ethyl propionate)-thio oxazole. After a few days the oil solidified to give a powder having a melting point of 38°–40° C. Yield 70%.

EXAMPLE 9

4,5-diphenyl-2-(2-ethyl oleate)-thio oxazole

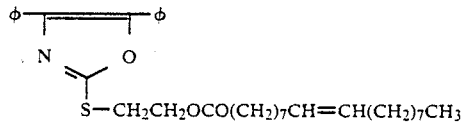

10 g of 4,5-diphenyl-2-(2-hydroxyethyl)-thio oxazole were dissolved in 10 ml of anhydrous acetone. 10 g of oleyl chloride and 4 g of triethylamine were added to the solution. At the end of the reaction, after one hour, the solution was filtered and concentrated, and the product purified by silica gel chromatography as described in the preceding examples. A yellow oil was obtained consisting of 4,5-diphenyl-2-(2-ethyl oleate)thio oxazole. Yield 70%.

The products of the present invention have pharmacological properties which are very similar to those of the starting compounds, that is, anti-inflammatory and anti-platelet-aggregative properties. The anti-inflammatory properties of 4,5-diphenyl-2-bis-(2-hydroxyethyl)-amino oxazole, known under the trade name of "Ditazole", have been reported by L. Caprino, F. Borrelli, R. Falchetti, Drug Res., 23, (9), 1272 (1973).

The derivatives of the present invention, however, have many other valuable properties which are not possessed, or are possessed only to a reduced extent, by the starting compounds, such as, for example, solubility in aqueous media, compatibility with synthetic polymers or with additives and plasticizers for said polymers, and solubility in fatty substances. Therefore, the pharmacological products based on said derivatives can advantageously be used in situations in which the original starting compounds could not be used.

When tested on platelet-rich-plasma according to the test method described by L. Caprino et al., op. cit., page 1277, Ditazole, its monoacetate ester and its diacetate ester were all found to possess similar antiplatelet-aggregative properties.

The three compounds, however, when physically admixed with cellulose triacetate fibers, modify their own anti-inflammatory properties to a different degree. For example, if fibers containing the three test compounds respectively, are introduced under the skin in rabbits, it has been found that, after a period of stay of the fibers in the test animals' bodies, only the fibers which contained pure Ditazole were removed unaffected, whereas the other fibers had been destroyed by the inflammatory action on the tissue. All this in spite of the fact that the anti-inflammatory properties of Ditazole as such are well known.

Another example in which the esters of the present invention find a useful application is in PVC tubing and other articles for pharmacological uses. Such articles can be obtained by extruding PVC compounds containing conventional plasticizers and small amounts of one or more of the esters of the present invention. Fatty acid esters, such as the oleate, are preferred since they also effect a plasticizing action on the PVC. Articles thus obtained show an improved compatibility with human blood.

We claim:

1. A method of treating inflammation pain and/or platelet aggregation in mammals including human beings by administering to an afflicted animal an effective dose in the range of 100 mg/kg to 500 mg/kg, based on the body weight, of a compound of the formula:

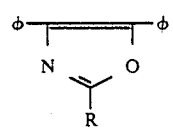

wherein R is a mono or bihydroxyalkyl substituted amino group or a mono hydroxyalkyl substituted thio group in which one or more available hydroxyl groups have been esterified with an acid containing 2-18 carbon atoms.

2. A method of treating inflammation, pain and/or platelet aggregation according to claim 1 wherein the hydroxyl group is esterified with an acid containing 2-9 carbon atoms.

3. A method of treating inflammation, pain and/or platelet aggregation according to claim 1 wherein the compound is:

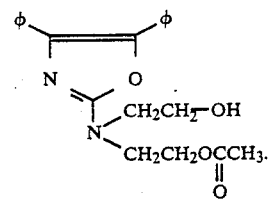

4. A method of treating inflammation, pain and/or platelet aggregation according to claim 1 wherein the compound is:

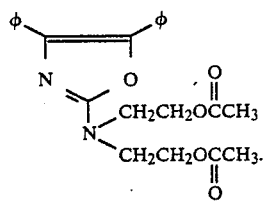

5. A method of treating inflammation, pain and/or platelet aggregation in mammals including human beings by administering to an afflicted mammal, in the presence of polymers selected from the group comprising cellulose triacetate and polyvinyl chlorides, an effective dose, in the range of 100 mg/kg to 500 mg/kg, based on the body weight, of a compound of the formula:

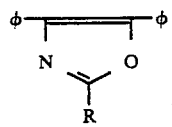

wherein R is a mono or bihydroxyalkyl substituted amino group or a mono hydroxyalkyl substituted thio group in which one or more available hydroxyl groups have been esterified with an acid containing 2-18 carbon atoms.

6. A method of treating inflammation, pain and/or platelet aggregation according to claim 5 wherein the hydroxyl group is esterified with an acid containing 2-9 carbon atoms.

7. A method of treating inflammation, pain and/or platelet aggregation according to claim 5 wherein the compound is:

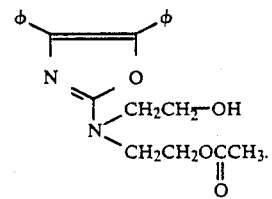

8. A method of treating inflammation, pain and/or platelet aggregation according to claim 5 wherein the compound is:

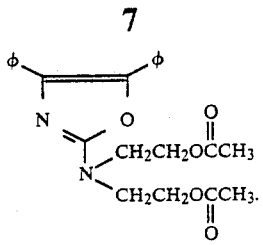
7
* * * * *
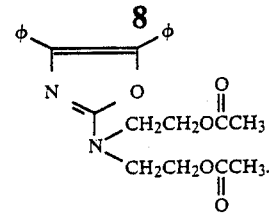
8
* * * * *